(12) United States Patent
Oehmen

(10) Patent No.: US 6,423,884 B1
(45) Date of Patent: *Jul. 23, 2002

(54) ABSORBENT ARTICLE HAVING APERTURES FOR FECAL MATERIAL

(75) Inventor: Heidi Ann Oehmen, Neenah, WI (US)

(73) Assignee: Kimberly-Clark Worldwide, Inc., Neenah, WI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/730,648

(22) Filed: Oct. 11, 1996

(51) Int. Cl.⁷ .............................. A61F 13/18; A61F 13/20
(52) U.S. Cl. ..................... 604/369; 604/373; 604/374; 604/378; 604/385.01; 604/385.101; 604/385.19
(58) Field of Search .................. 604/369, 373, 604/378–385.2, 393–396, 385.01, 385.101, 385.19

(56) References Cited

U.S. PATENT DOCUMENTS

| | | | |
|---|---|---|---|
| 3,038,215 A | 6/1962 | Harwood | 19/161 |
| 3,344,789 A | 10/1967 | Arnold et al. | |
| 3,559,648 A | 2/1971 | Mason, Jr. | |
| 3,572,342 A * | 3/1971 | Lindquist et al. | 604/369 |
| 3,593,717 A * | 7/1971 | Jones, Sr. | 604/373 |
| 3,654,060 A | 4/1972 | Goldman | 161/112 |
| 3,756,907 A | 9/1973 | Heling | 162/114 |

(List continued on next page.)

FOREIGN PATENT DOCUMENTS

| | | | |
|---|---|---|---|
| EP | 0165807 | 12/1985 | |
| EP | 0 165 807 | * 12/1985 | |
| EP | 0 486 006 | 5/1992 | |
| EP | 0561023 | * 9/1993 | 604/385.2 |
| EP | 0 626 160 | * 11/1994 | |
| EP | 0 631 767 | 1/1995 | |
| GB | 2 275 611 | 9/1994 | |
| GB | 2 297 474 | 8/1996 | |
| JP | 4-150853 | * 5/1992 | |
| JP | 5-269168 | 10/1993 | |
| JP | 6-504700 | 6/1994 | |
| JP | 7-88132 | 4/1995 | |
| WO | 92/15269 | 9/1992 | |
| WO | 96/09026 | 3/1996 | |

OTHER PUBLICATIONS

Translation of Japanese 4–150,853.*

*Primary Examiner*—John G. Weiss
*Assistant Examiner*—K. M. Reichle
(74) *Attorney, Agent, or Firm*—Wilhelm Law Service; Thomas D. Wilhelm

(57) ABSTRACT

An absorbent article includes an outer cover and a bodyside liner. A fecal retaining structure having at least one aperture is mounted in the rear portion of the absorbent article. The retaining structure has at least one, preferably multiple, apertures sized to retain exudates from a typical bowel movement and to displace such exudates from the skin of the user. The fecal retaining structure preferably has a surface layer on the outer surface which contacts the body of the user. The surface layer has a slick surface that assists in moving fecal material into the apertures. An absorbent core may be mounted in the absorbent article, especially in the front portion of the absorbent article.

18 Claims, 4 Drawing Sheets

U.S. PATENT DOCUMENTS

| | | | |
|---|---|---|---|
| 3,927,673 A | | 12/1975 | Taylor |
| 4,173,046 A | * | 11/1979 | Gallagher |
| T990,006 I4 | | 1/1980 | Williams .................... 423/131 |
| 4,377,544 A | | 3/1983 | Rasmussen ................ 264/139 |
| 4,469,734 A | | 9/1984 | Minto et al. ................ 428/134 |
| 4,560,372 A | | 12/1985 | Pieniak ....................... 604/369 |
| 4,588,630 A | | 5/1986 | Shimalla .................... 428/131 |
| 4,673,402 A | * | 6/1987 | Weisman et al. |
| 4,704,112 A | | 11/1987 | Suzuki et al. .............. 604/378 |
| 4,753,646 A | * | 6/1988 | Enloe ......................... 604/378 |
| 4,791,685 A | | 12/1988 | Maibauer ........................ 2/227 |
| 4,798,603 A | * | 1/1989 | Meyer et al. ............... 604/378 |
| 4,834,737 A | | 5/1989 | Khan |
| 4,842,794 A | | 6/1989 | Hovis et al. ................ 264/145 |
| 4,968,312 A | | 11/1990 | Khan |
| 4,990,147 A | * | 2/1991 | Freeland .................... 604/393 |
| 5,342,338 A | * | 8/1994 | Roe |
| 5,383,867 A | | 1/1995 | Klinger |
| 5,397,316 A | * | 3/1995 | LaVon et al. |
| 5,397,318 A | * | 3/1995 | Drier |
| 5,405,342 A | * | 4/1995 | Roessler et al. ............ 604/394 |
| 5,415,640 A | | 5/1995 | Kirby et al. ................ 604/383 |
| 5,439,458 A | * | 8/1995 | Noel et al. |
| 5,558,660 A | * | 9/1996 | Drier ........................... 604/578 |

* cited by examiner

ABSORBENT ARTICLE HAVING APERTURES FOR FECAL MATERIAL

FIELD OF THE INVENTION

Absorbent articles such as infant diapers, training pants, adult incontinence products, and the like are well known. Such articles have achieved a wide acceptance due to their ability to receive and absorb body exudates.

This invention pertains to an absorbent article for containing body exudates. This invention utilizes a fecal material retaining structure having at least one, and preferably multiple apertures to receive and retain exudates, and especially fecal material.

BACKGROUND OF THE INVENTION

In general, body exudates of urine and fecal material should be received and retained by the absorbent article. However, leakage problems are common, especially of liquidous or semi-liquidous fecal material. Furthermore, even if fecal material does not leak, it can have an adverse impact on the skin of the user or wearer of an absorbent article.

Typically, fecal material is received at the surface of the bodyside liner. Mobile liquid contained in the fecal material may be absorbed through the bodyside liner, into an absorbent core of the absorbent article, and thus moved away from the skin of the user. However, in most cases the solids portion of fecal material, along with any liquid which is immobilized in the solids portion, generally remains at the surface of the bodyside liner, incapable of penetrating through the bodyside liner and moving away from the skin of the user. In such cases, the solid portion of the fecal material typically remains trapped at the outside surface of the bodyside liner, between the bodyside liner and the skin of the user. During normal usage the fecal material can spread outwardly along the outside surface of the bodyside liner and cover an increased area of the skin of the user.

Some attempts have been made to remove the fecal material from the skin of the user. For example, one absorbent article includes a single large hole aligned between the buttocks of a user. The single hole opens into a containment chamber to contain and store exudates, and especially fecal material. However, the single large hole is not held or otherwise fixed in its location with respect to the anus of the user.

U.S. Pat. No. 5,342,338 to Roe discloses small apertures in the bodyside liner of an absorbent article to dewater fecal material. However, little if any of the fecal material is displaced from the skin of the user.

SUMMARY OF THE DISCLOSURE

In the present invention, an absorbent article displaces fecal material from the skin of the user, and thereby reduces the amount of contact between the fecal material and the skin of the user or wearer of the absorbent article. Absorbent articles of the invention use an apertured retaining structure placed in the rear portion of the absorbent article to control placement of the fecal material. A slick outer surface utilizes the pressure of the body of the user on the retaining structure, in combination with sliding movement between the outer surface and the body of the user, to move fecal material into the apertures and away from the skin. Use of the retaining structure provides easier clean up of the skin of the user after the absorbent article is soiled. Additionally, fecal material is prevented from spreading to the front portion of the absorbent article and contaminating other parts of the body of the user.

In one embodiment, the absorbent article has a length, a front portion, a rear portion, a crotch portion connecting the front and rear portions, and a central axis perpendicular to the length of the absorbent article. The central axis extends across the crotch portion and divides the absorbent article into two sections of approximately equal length. The absorbent article comprises a chassis having an outer cover, and a bodyside liner mounted in facing relationship to the outer cover and contacting the body of the user in the front portion of the absorbent article. The absorbent article includes an absorbent core located between the bodyside liner and the outer cover in the front portion of the absorbent article, and not in the rear portion; and a fecal material retaining structure mounted to the chassis in the rear portion of the absorbent article and contacting the body of the user. Edges of apertures of the fecal material retaining structure are generally in direct contact with the body of the user.

In another embodiment, the fecal material retaining structure comprises at least a first layer of a highly absorbent material such as cellulosic pulp, and at least a second layer of resiliently compressible surge material.

In another embodiment, an outer surface layer forms the outer surface of the fecal retaining structure: The surface layer has a hydrophobic, slick outer surface for contacting the body of the user and facilitating movement of fecal material material into at least one aperture. The surface layer has a critical surface tension for wetting that preferably is less than the critical surface tension for wetting of fecal material from a breast fed infant. The critical surface tension for wetting of the surface layer is typically less than about 50 dynes/centimeter, and preferably is about 30 dynes/centimeter, to assist with moving the fecal material of a breast fed infant into one or more apertures in the fecal material retaining structure.

In other embodiments, the fecal material retaining structure has at least one aperture penetrating the first and second layers of the fecal material retaining structure. The at least one aperture preferably has a volume between about 14 cubic centimeters and about 26 cubic centimeters at rest. The combined uncompressed thickness of first and second layers adjacent at least one aperture is between about 0.5 inch and about 1.0 inch. An at least one large aperture preferably comprises multiple apertures covering between about 40% and about 60% of the surface area of the fecal material retaining structure. A surface area of the fecal material retaining structure is defined as that area bounded by a perimeter within which the fecal material retaining structure contacts the body of the user. The surface area of each of the large apertures in the absorbent article preferably is at least 5 square centimeters.

The apertures can have a tear-drop shape, a circular shape, an elliptical shape, a diamond shape or other shape or shapes. The large tear-drop shaped aperture preferably has a greatest width of about 1.5 inch and a greatest length of about 2 inches.

In some embodiments, a front edge of the fecal material retaining structure extends from about 0.5 inch to about 2 inches frontwardly in the absorbent article beyond the central axis. The width of the fecal material retaining structure can substantially equal the width of the absorbent core in the front portion of the absorbent article.

In some embodiments, a support layer of absorbent material is located between the fecal material retaining structure and the chassis. Fecal material moves through the apertures to contact the support layer. The support layer receives liquid from the fecal material, and preferably swells no more than about 13% upon absorption of body exudates. The support layer preferably comprises a fibrous cellulosic pulp having a basis weight of between about 90 grams per square meter and about 140 grams per square meter. The layer of absorbent material has an absorption capacity ratio of between about 6 grams and about 10 grams of liquid exudates per gram of material.

In another embodiment, at least two apertures extend through at least the first and second layers of the fecal material retaining structure to receive and retain fecal material. The apertures preferably have an overall volume of at least 140 cubic centimeters at rest and are arranged and configured to conform to the body of the user. Larger apertures are preferably sized to retain fecal material having a thickness greater than about 0.5 inch. Smaller apertures provide enhanced flexibility to the fecal material retaining structure.

In some embodiments, at least one first layer of a first material is secured to the surface layer, at least one second layer of a second material is secured to the first layer, and at least two apertures are formed in the surface layer. The first and second layers and the at least two apertures receive and retain fecal material.

In yet another embodiment, the first layer comprises multiple layer elements of the first material and/or the second layer comprises multiple layer elements of the second material, the multiple layer elements being interleaved and respectively secured to one another.

Figure 1:
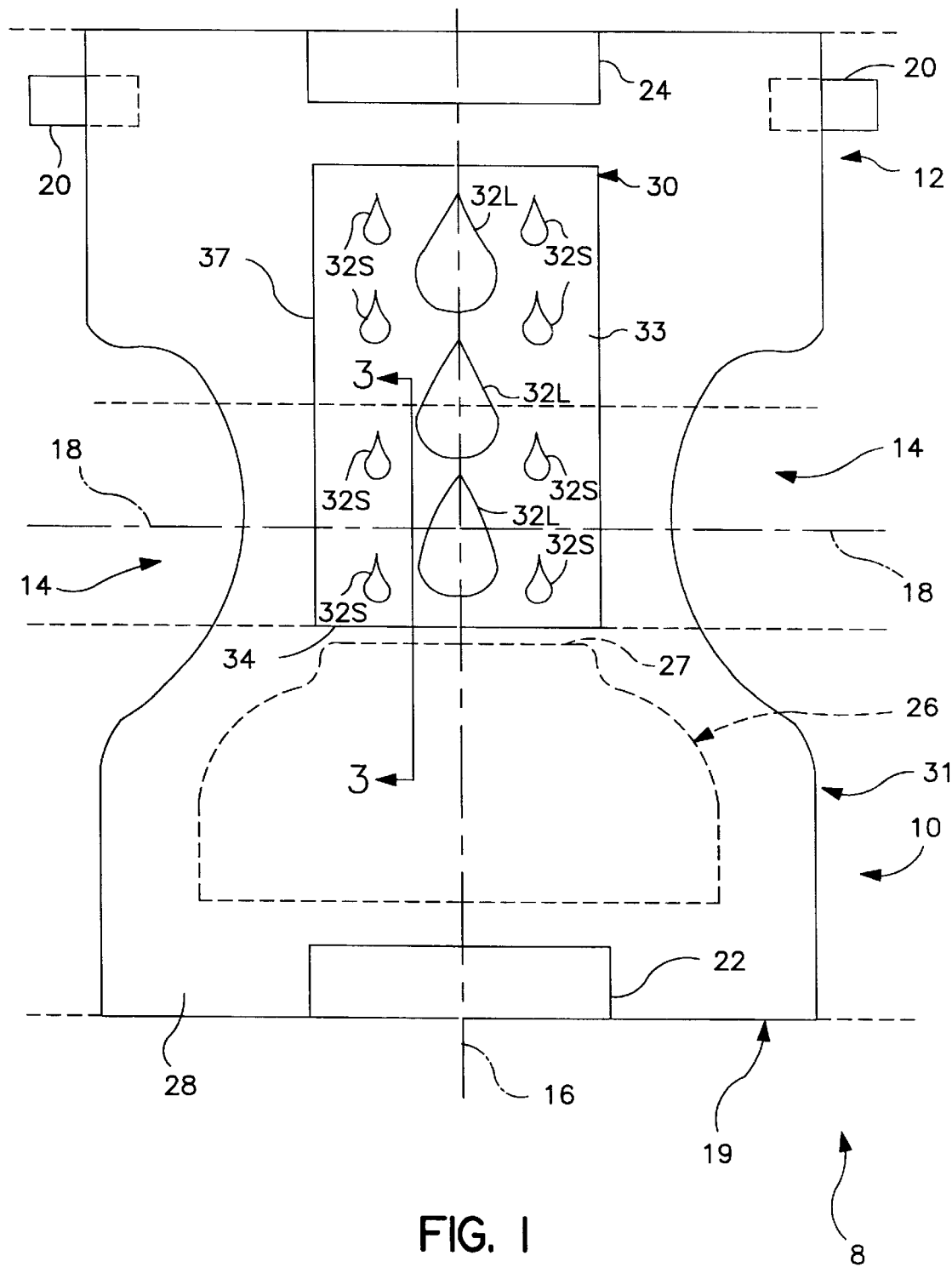
FIG. 1 shows a top view of a first absorbent article of the invention.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

The present invention relates to absorbent articles designed to capture and contain body exudates. While the preferred embodiments of the present invention are described herein in terms of an absorbent article such as a diaper for an infant, the invention includes, and is equally applicable to, adult incontinent briefs, training pants and the like.

The present invention can best be understood by reference to the drawings. FIG. 1 illustrates an absorbent article 8 including a front portion 10, a rear portion 12 and a crotch portion 14. A longitudinal axis 16 extends through front portion 10, rear portion 12 and crotch portion 14 along the length of absorbent article 8. A transverse central axis 18 is perpendicular to the length of absorbent article 8. Transverse central axis 18 is centered in, and extends across, crotch portion 14. Transverse central axis 18 thus divides the absorbent article into two sections of approximately equal length.

Figure 3:
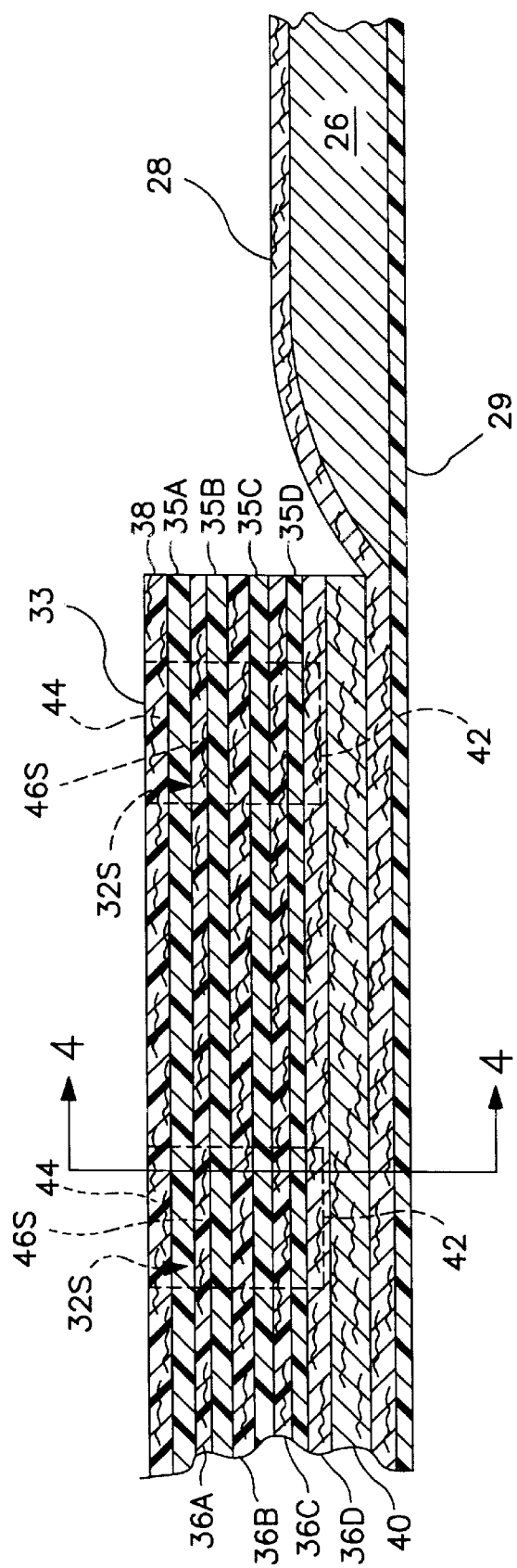
FIG. 3 shows a cross-section of a portion of the first absorbent article and is taken at 3—3 in FIG. 1.

As illustrated, absorbent article 8 includes attachment ears 20, front waist elastomeric element 22, rear waist elastomeric element 24 and absorbent core 26 mounted between bodyside liner 28 and outer cover 29. Outer cover 29 extends under or below bodyside liner 28, absorbent core 26 and fecal material retaining structure 30. Such positioning of outer cover 29 is shown in FIG. 3. Chassis 31, indicated in FIG. 1, comprises the combination of outer cover 29 and bodyside liner 28.

Fecal retaining structure 30 includes multiple apertures 32S, 32L that receive fecal material material, and retain or store the fecal material away from the body of the user or wearer of the absorbent article 8. FIG. 1 shows apertures 32S, 32L as teardrop shaped openings in retaining structure 30. Outer surface 33 of retaining structure 30 preferably is a slick surface.

Figure 2:
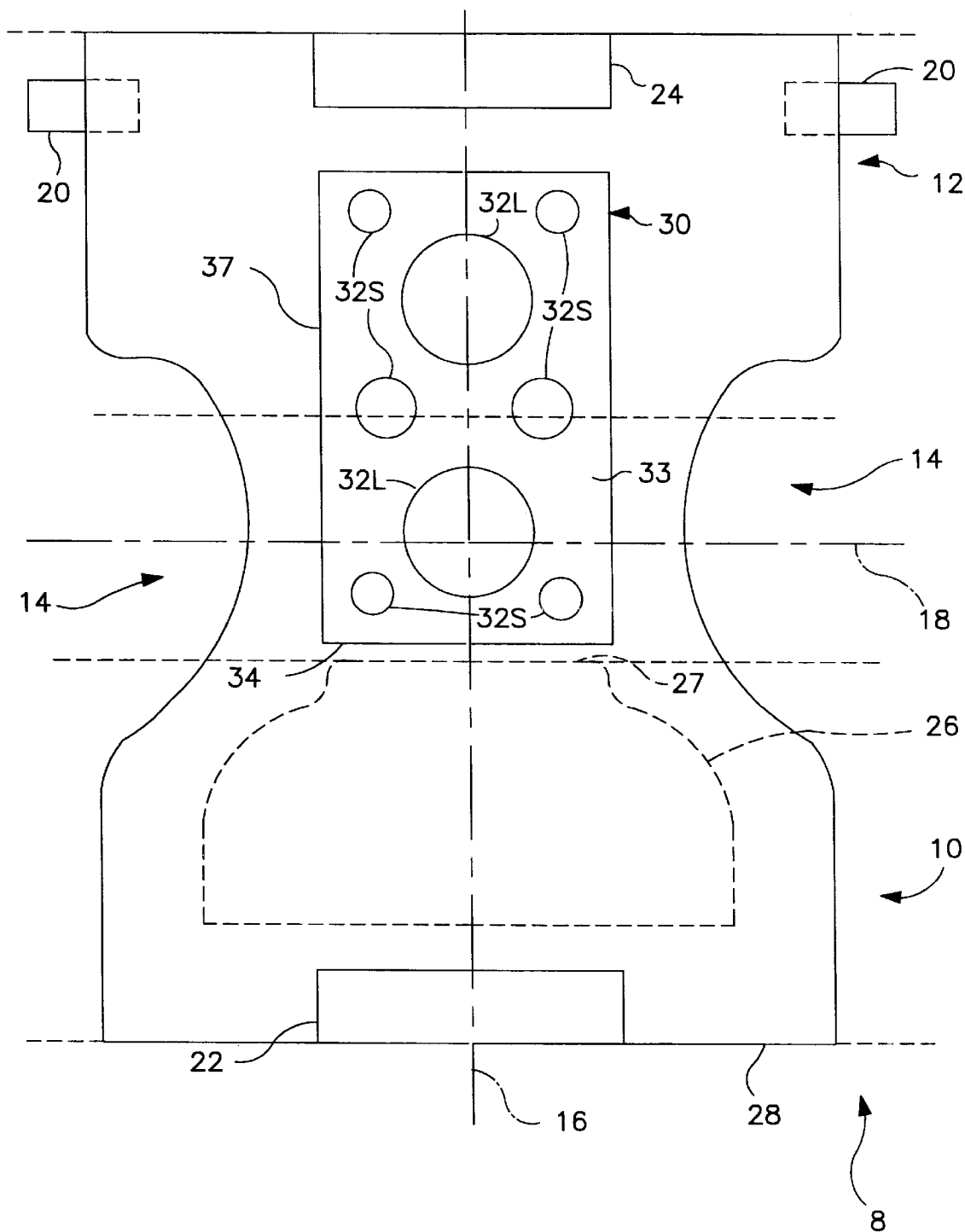
FIG. 2 shows a top view of a second absorbent article of the invention.

FIG. 2 illustrates a similar embodiment to that set forth in FIG. 1, except that apertures 32S, 32L have a circular shape and different total number.

Absorbent article 8 in FIG. 1 is applied to the body of a user by securing attachment ears 20 on rear portion 12 to a securement surface (not shown) on outer cover 29 of front portion 10. Attachment ears 20 can comprise the hooks of a hook and loop fastening system. The securement surface then typically comprises a corresponding loop material attached to outer cover 29 in front portion 10 and adapted to releasably engage with the hook material. Other well known fastening means can also be used to support absorbent article 8 upon the user. For example, a cohesive system, an adhesive fastener system or the like may also be utilized to fasten absorbent article 8.

Rear waist elastomeric element 24 and front waist elastomeric element 22 provide retractive forces urging retainment of absorbent article 8 to the body of the user. Elastomeric elements 22, 24 can be formed from materials which are attached to outer cover 29 and/or bodyside liner 28. Suitable materials include strands, ribbons or one or more layers of a polymeric and/or elastomeric material which may be adhered or otherwise mounted to absorbent article 8 while in a stretched position. Alternatively, the material can be attached, in a relaxed condition, to the absorbent article 8 while front portion 10 and/or rear portion 12 of absorbent article 8 is pleated. Other arrangements providing retractive force in the waist of absorbent article 8 are also contemplated by the invention.

As illustrated in FIG. 1, absorbent core 26 may be located within the front half of absorbent article 8 between transverse central axis 18 and a front edge 19 of the absorbent article 8. Preferably absorbent core 26 is confined within front portion 10 of absorbent article 8. At this location, as shown in FIG. 1, absorbent core 26 absorbs liquids such as, for example, urine, from the body of the user while retaining structure 30 retains fecal material.

Absorbent core 26 suitably comprises a relatively thicker structure, compared to outer cover 29 and bodyside liner 28, and includes a matrix of hydrophilic fibers, such as a web of cellulosic fluff, preferably in combination with a high-absorbency material commonly known as superabsorbent material. In a particular embodiment, absorbent core 26 comprises a mixture of superabsorbent hydrogel-forming particles and wood pulp fluff. In place of the wood pulp fluff, one may use synthetic, polymeric, meltblown fibers or a combination of meltblown fibers and natural fibers. The superabsorbent material may be substantially homogeneously mixed with the hydrophilic fibers or may be otherwise combined into the absorbent core.

Alternatively, absorbent core 26 may comprise a laminate of fibrous webs and superabsorbent material or other suitable means of maintaining a superabsorbent material in a localized area.

Absorbent core 26 can have any of a number of shapes. For example, the absorbent core may be rectangular, oval-shaped or the shape shown in FIG. 1. The relatively thicker structure of absorbent core 26 generally does not extend over the entire dimensions of outer cover 29 or bodyside liner 28. Typically, absorbent core 26 is confined to front portion 10 of absorbent article 8. While absorbent core 26 can extend under fecal material retaining structure 30, typically such absorbent core has a thicker front portion, and a thinner rear portion under fecal material retaining structure 30. Absorbent core 26 preferably has a width at edge 27 thereof, substantially equal to the width of fecal material retaining structure 30.

The superabsorbent material in absorbent core 26 can be selected from among natural, synthetic and modified natural polymers and materials. The high absorbency materials can be inorganic materials, such as silica gels, or organic compounds, such as crosslinked polymers. The term crosslinked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

Bodyside liner 28 covers absorbent core 26 in front portion 10 of absorbent article 8. Bodyside liner 28 preferably is located dominantly, if not only, in front portion 10 and not dominantly in rear portion 12. Bodyside liner 28 can extend into crotch portion 14 and rear portion 12 of absorbent article 8, but bodyside liner 28 generally does not cover fecal material retaining structure 30 at apertures 32. Rather, over the area of chassis 31 which is covered by fecal material retaining structure 30, absorbent article 8 is configured such that contact between absorbent article 8 and the body of the user occurs at outer surface 33.

A suitable bodyside liner 28 may be manufactured from a wide selection of web materials, such as porous foams, reticulated foams, apertured plastic films or natural or synthetic fibers. For example, bodyside liner 28 may comprise wood or cotton fibers. Other possible materials are synthetic fibers, such as polyester or polypropylene fibers, or a combination of natural and synthetic fibers. Bodyside liner 28 is suitably utilized to help isolate the liquids held in absorbent core 26 from the skin of the wearer.

In addition, various woven and nonwoven fabrics can be used for bodyside liner 28. For example, bodyside liner layer 28 may be composed of a meltblown or spunbonded web of polyolefin fibers. Bodyside liner 28 may also comprise a carded and/or bonded web composed of natural and/or synthetic fibers. Bodyside liner 28 may also be composed of a substantially hydrophobic material wherein the hydrophobic material is treated with a surfactant or otherwise processed to impart a desired level of wettability and hydrophilicity. In a particular embodiment of the present invention, bodyside liner layer 28 may comprise a spunbonded polypropylene fabric composed of about 2.8–3.2 denier fibers formed into a web having a basis weight of about 22 grams per square meter and a density of about 0.06 grams per cubic centimeter. The fabric is treated with about 0.3 weight percent of a surfactant. Bodyside liner 28 may comprise a multiplicity of components, layers, or partial layers, which correspond to any of the materials disclosed herein, as well as others known in the art.

Outer cover 29 can be formed from a single layer, or from multiple components, layers, or partial layers, of material, such that the resulting outer cover is substantially impermeable to liquids. A typical outer cover 29 may be manufactured from a thin plastic film or other flexible liquid-impermeable material. For example, outer cover 29 can be formed from a polyethylene film having a thickness of from about 0.012 millimeters to about 0.051 millimeters. When it is desirable that outer cover 29 have a more clothlike feeling, it may comprise, for example, a polyethylene film laminated to a surface of a nonwoven web, such as a spunbonded web of polyolefin fibers. For example, a polyethylene film having a thickness of about 0.015 millimeters may have thermally or otherwise laminated thereto a spunbonded web of polyolefin fibers having a thickness from 1.5 to 2.5 denier per filament, which nonwoven web has a basis weight of about 24 grams per square meter. Further, outer cover 29 can be formed of a woven or nonwoven fibrous web which has been totally or partially constructed or treated to impart a desired level of liquid impermeability to selected regions that are adjacent or proximate the absorbent core 26. Still further, outer cover 29 may optionally be composed of a microporous material which permits vapors to escape from absorbent core 26 and through outer cover 29 while preventing liquid exudates from passing through the outer cover.

Fecal material retaining structure 30 contains at least one aperture 32S, 32L, and preferably a plurality of apertures to retain fecal material away from the body of the user. While any number of apertures can be used, preferably 2 to 20 apertures, and more preferably 8 to 17 apertures are provided in retaining structure 30. The number of apertures, the spacing between apertures, and the sizes of the apertures, can be varied. As illustrated in FIG. 3, each aperture 32S has a bottom 42 at support layer 40 and an opposing top 44 at the outer surface 33 for abutting the body of a wearer.

As shown in FIGS. 1 and 2, especially the larger central apertures 32L are specifically designed and configured to receive and retain fecal material. While smaller apertures 32S receive and retain some fecal material, their primary function is to increase and improve the overall flexibility and resiliency of retaining structure 30. Outer surface 33 of retaining structure 30 is slick, and thus allows fecal material to be readily moved along the surface and into apertures 32. Larger central apertures 32L preferably have an open surface area of at least 5 square centimeters. The larger size apertures 32L are preferred for their capacity to retain the necessary quantities of exudates.

The larger teardrop shaped apertures 32L of FIG. 1 preferably have greatest widths of about 1.5 inches and greatest lengths of about 2 inches. The larger circular apertures 32L of FIG. 2 preferably have diameters of about 1 inch. Therefore, larger apertures 32L shown in FIGS. 1 and 2 have surface areas of at least about 5 square centimeters. Other shapes for apertures 32 include, but are not limited to diamond-shaped, oval, elliptical, and hexagonal shapes or the like. Apertures 32 preferably comprise from about 25% to about 75%, and more preferably about 40% to about 60%, and most preferably comprise about 50% of the area of a surface of fecal material retaining structure 30 as defined within outer perimeter 37 of retaining structure 30. Apertures 32L are large enough to retain fecal material and have a thickness greater than about 0.5 inch.

The pattern of apertures 32 preferably includes large apertures 32L in a target region along the length of longitudinal axis 16 in rear portion 12 and crotch portion 14 of absorbent article 8. Preferably two to four apertures comprise large apertures 32L in the target region. Other patterns or arrangements are contemplated herein. For instance, smaller apertures 32S can be located between larger apertures 32L and on opposing sides of, or upon, longitudinal axis 16.

Layers 35, 36 and 38 adjacent aperture 32S, 32L preferably have a thickness of between about 0.5 inch and 1.0 inch at rest corresponding to the depth of aperture 32S, 32L. Larger depths are possible, but a depth of at least about 0.38 inch to about 0.5 inch is, generally required so that apertures 32S, 32L adjacent layers 35, 36 and 38 effectively receive and retain fecal material displaced from the skin of the user. Larger depths of apertures 32 can create a problem with respect to the overall bulkiness of absorbent article 8. At lesser depths, apertures 32S, 32L are less effective at keeping the fecal material displaced from the skin of the user. Apertures 32S, 32L preferably extend through layers 35, 36, 38 to support layer 40.

Each larger aperture 32L along longitudinal axis 16 preferably has an open containment volume of at least about 20 cubic centimeters at rest. Furthermore, multiple apertures 32S, 32L in combination, have depths and areas defining sufficient open containment volumes 46S, 46L (not shown), respectively 46L (not shown), volume and structure to receive and retain therein an amount of fecal material representing a typical bowel movement of a typical user. All apertures 32S, 32L of a fecal material retaining structure 30 preferably have, in combination, a total volume of at least about 140 cubic centimeters. All the apertures 32S, 32L in a given fecal material retaining structure 30 preferably have the same depth, but variations in depth, especially of the smaller apertures, are permissible.

Front edge 34 of fecal material retaining structure 30 extends from about 0.5 inch to about 2 inches, and. preferably about 1.5 inches, frontwardly into the crotch portion beyond central transverse axis 18 and toward front portion 10 of absorbent article 8. This forward location of front edge 34 is important so fecal material retaining structure 30 can collect and retain substantial amounts of fecal material in the target area.

Figure 4:
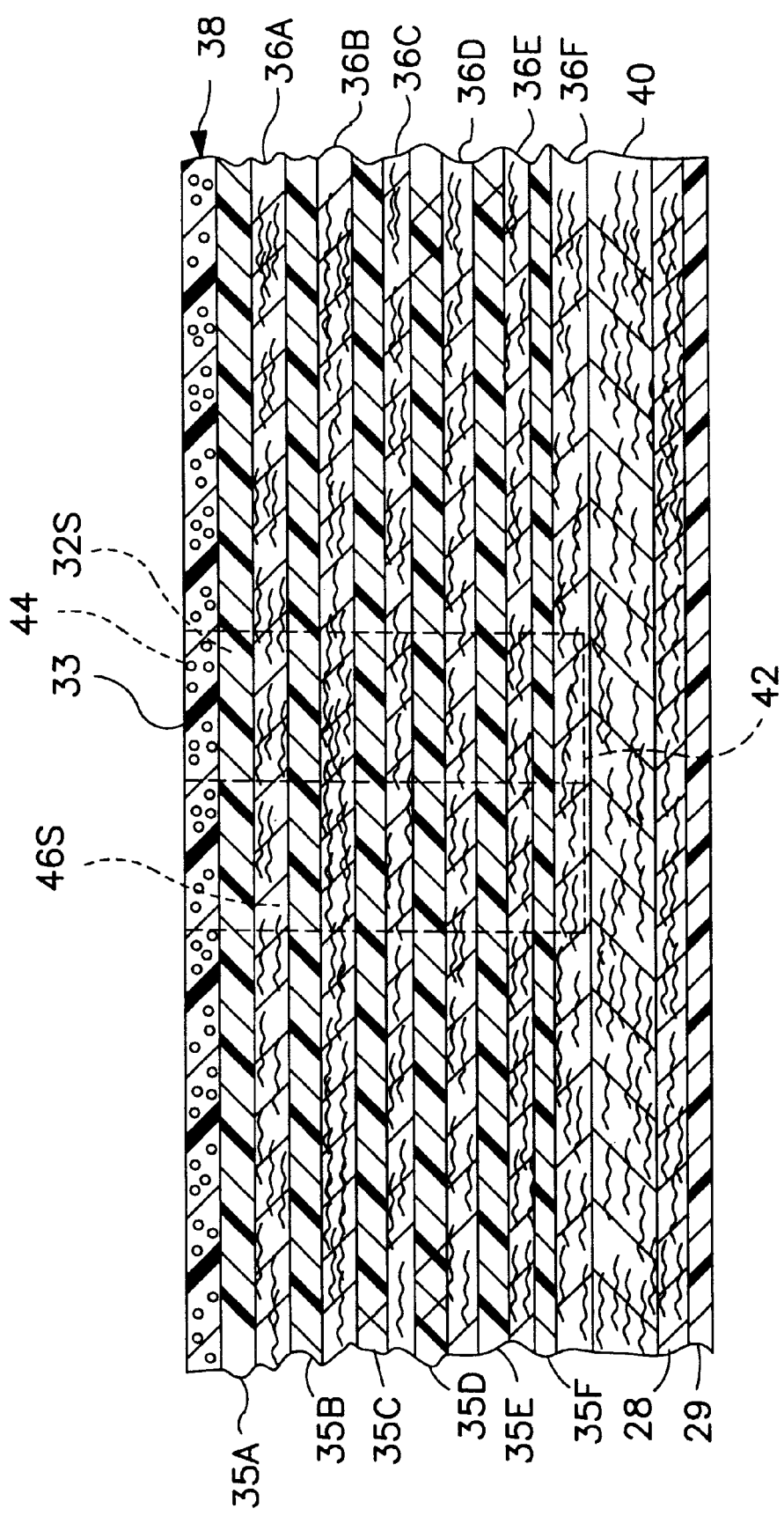
FIG. 4 shows a cross-sectional cutaway view of a fecal material retaining structure of the invention.

The elements of fecal material retaining structure 30 are illustrated in FIGS. 3 and 4. As illustrated, fecal material retaining structure 30 may include layers 35A–35F of surge material and layers 36A–36F of cellulosic pulp, preferably uncreped through air-dried bleached chemical thermal mechanical pulp., Layers 35, 36 preferably are alternated or interleaved. Fecal material retaining structure 30 may further include outer surface layer 38, including outer surface 33 that contacts the body of the user. Support layer 40 underlies the combination of surge layers 35 and pulp layers 36.

In a preferred embodiment, surge layers 35 comprise 70% by weight of ten denier sheath/core bicomponent polyethylene/polyethylene terephthalate fiber and 30% by weight of three denier sheath/core bicomponent polyethylene/polypropylene fiber. Each surge layer 35 preferably has a weight of about 150 grams per square meter and a thickness of about 3 millimeters. Surge layers 35 provide compression resistance when absorbent article 8 is applied to the body of a user, to thus maintain the volumes in apertures 32S, 32L. Other possible surge layers having materials which can function in the invention are set forth in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, and filed Mar. 4, 1994 (Attorney docket No. 11,256); and U.S. patent application Ser. No. 206,069 of C. Ellis and R. Everett, entitled, IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No. 11,387); the disclosures of both of which are hereby incorporated by reference. Furthermore, other surge materials having the desired compression resistance and other similar desired properties can be used.

In a preferred embodiment, layers of material 36A–36F generally comprise cellulosic pulp. Layers 36 preferably comprise uncreped through air-dried bleached chemical thermal mechanical pulp that is formed by combining wood fibers with a wet strength resin in creating a higher-strength web, and drying the resulting web in what is commonly referred to as an uncreped through drying process. Additional details regarding layers 36 are set forth in U.S. patent application Ser. No. 08/226,735 by Wendt et al. entitled "Method of Making Soft Tissue Products" filed Apr. 12, 1994, the disclosure of which is hereby incorporated by reference. Preferred layers 36 have a basis weight of about 60 grams per square meter. Other materials with suitable or similar compression and resilience characteristics can also be used in place of cellulosic pulp.

Layers 35, 36 preferably are stratified or alternated as shown in FIG. 4. Alternating the layers improves the compression and compression recovery of retaining structure 30 as well as flexibility and resilience. Surge layers 35 provide the desired resilience and compression recovery and layers 36 provide a wicking effect for storage of minimal amounts of liquid. However, other arrangements are contemplated by the invention. For instance, a third layer of material (not shown) having desired characteristics could be interleaved with layers 35, 36. In addition, layers 35, 36 in FIG. 4 can be reversed so that a cellulosic pulp layer 36 contacts outer surface layer 38. Similarly, a surge layer 35 can contact bottom support layer 40. Furthermore, a single composite material having the desired flexibility, compression recovery, and resilience properties could entirely replace any or all of the set of layers 35, 36 and 38.

Outer surface layer 38 contacts the body of the user. Surface layer 38 has a generally non-absorbent, slick outer surface 33 that facilitates movement of fecal material into apertures 32S, 32L. In use, the pressure between the body of the user and outer surface 33 of fecal material retaining structure 30 and to a degree in combination with lateral movement of the body with respect to outer surface 33, pushes fecal material into apertures 32S, 32L thus isolating the material from the body of the user. The end result is that the amount of fecal material contacting the skin of the user is reduced. A suitable surface layer 38 is a foam layer made by 3M Corp., St. Paul, Minn., as No. 1773. The 3M foam layer has a thickness of about 1/16 inch or 1 millimeter. Surface layer 38 preferably is comprised of polyethylene, coated or otherwise joined with a layer of pressure-sensitive adhesive such as an acrylate. Approximately 0.8 millimeters is the preferred thickness of the foam material and 0.2 millimeters is the preferred thickness of adhesive. Surface layer 38 has a hydrophobic, slick outer surface 33 for contacting the body of the user, and facilitating movement of fecal material into apertures 32S, 32L.

Other materials having similar surface characteristics as the foam layer can also be utilized. Exemplary materials that can be used include polyethylene, polypropylene, polyurethane, polyester and rubber-based materials. Other pliable materials having similar properties can also be utilized.

In embodiments where the exudates comprise low viscosity fluids, such as fecal material from only breast fed infants, outer surface layer 38 preferably has a critical surface tension for wetting less than the critical surface tension for wetting of urine or the fecal material. Thus, urine and fecal material from a breast fed infant are readily released by outer surface 33. The critical surface tension for wetting of urine or fecal material from a breast fed infant is generally about 50 to about 60 dynes/centimeter.

Surface layer 38 most preferably has a critical surface tension for wetting of about 30 dynes/centimeter. Other surface layers made with foams or materials with similar properties may also be utilized as the material defining outer surface 33. As long as the critical surface tension for wetting of outer surface layer 38 is less than the critical surface tension for wetting of the fecal material from breast fed infant, the surface layer will not deleteriously wet out or absorb the body exudate liquid. Hence, surface layer 38 assists the movement of fecal material into apertures 32S, 32L.

Other layers of material, such as film or the like, having a similar critical surface tension for wetting and slickness can be utilized in place of surface layer 38 in the embodiment where the exudates are from breast fed infants. Infants eating food and using formula have higher viscosity fecal material and the critical surface tension of wetting does not become a relevant factor in controlling the flow of fecal material.

Support layer 40 comprises a cellulosic pulp similar to layers 36, and preferably comprises an uncreped through air-dried bleached chemical thermal mechanical pulp. Bottom support layer 40, however, is heavier than a respective layer 36, having a preferred basis weight of between about 90 and about 140 grams per square meter, and most preferably about 105 grams per square meter. Support layer 40 preferably is through-dried to impart a fast wicking rate and high absorbent capacity. This tends to move a favorable amount of liquid exudate to layer 40 most remote from the skin of the user. With the liquid thus displaced from the body, the body is less likely to be wetted by such exudates, or to be wetted to a lesser degree. Support layer 40 preferably has an absorption capacity of between about 6 grams and about 10 grams of normal body liquid exudates per gram of material. Layers 35, 36, 40 preferably do not contain significant amounts of swellable superabsorbent.

Preferred support layer 40 has a thickness, when dry of about 0.024 inch. When preferred support layer 40 becomes saturated with liquid, its thickness increases to about 0.027 inch. The increase in thickness of support layer 40, when saturated, is preferably less than about 13%. Accordingly, such layers preferably can absorb body exudates to their respective capacities without deleterious swelling of such layers, and accompanying closure, or effective closure, of apertures 32 such swelling.

In contrast, a typical superabsorbent material, such as those described earlier with respect to absorbent core 26 have greater swelling when saturated with liquids. An exemplary superabsorbent pad having a thickness of 1.7 millimeters when dry, swells to 5.8 millimeters when saturated with liquid. The superabsorbent pad therefore increases in thickness by over 230%. Such an increase in thickness by support layer 40 would effectively render apertures 32S, 32L inoperable, or far less efficient, for retention of fecal material. Therefore, support layer 40 functions much differently than any type of superabsorbent material.

Layers 35A–35F, 36A–36F, 38 and 40, which form retaining structure 30, are secured to each other along their peripheries by adhesive, such as spray adhesive, or other securement systems. Furthermore, the respective layers are also preferably secured to each other by adhesive or the like at inner portions of retaining structure 30, in areas devoid of apertures 32S, 32L.

Apertures 32S, 32L can be formed in retaining structure 30 after the respective layers 35A–35F, 36A–36F, 38 and 40 are secured to each other. Apertures 32S, 32L preferably have walls extending through layers 35, 36 at a perpendicular to outer surface 33, thus to form cylindrical, tear-drop, or other shaped, constant cross-section apertures 32S, 32L. The cross-sections of apertures 32S, 32L can, in the alternative, vary with depth, whereby bottoms 42 of apertures 32S, 32L adjacent layer 40 may be rounded or tapered, or otherwise advantageously configured. Apertures 32S, 32L preferably are formed through all of layers 35, 36 and 38, but not through layer 40.

The relationship between bodyside liner 28, outer cover 29, absorbent core 26, and fecal material retaining structure 30 in preferred embodiments is more clearly shown in FIG. 3. As seen in FIG. 3, absorbent core 26 is located between outer cover 29 and bodyside liner 28 in at least the front portion 10 of absorbent article 8.

In some less preferred embodiments (not shown), absorbent core 26 extends under fecal material retaining structure 30. However, in such embodiments, that portion of absorbent core 26 which extends under fecal material retaining structure 30 preferably has a reduced thickness of no more than 50% of the greatest thickness of the absorbent core in front portion 10. The reduced thickness thereby limits the impact of the absorbent core on the overall thickness of the absorbent article 8 at the fecal material retaining structure.

Fecal material retaining structure 30 is mounted to chassis 31 such as at outer cover 29 in rear portion 12, and extends frontwardly to overlie at least part of crotch portion 14 of absorbent article 8. As seen in FIGS. 1 and 2, fecal material retaining structure 31 overlies chassis 31 over substantially the entirety of the center regions of rear portion 12 and crotch portion 14, on both sides of longitudinal axis 16.

Fecal material retaining structure 30 is secured to chassis 31 at e.g. outer cover 29 by adhesive or the like at the interface between layer 40 and the chassis. From layer 40, and as seen in FIG. 3, fecal material retaining structure 30 extends upwardly through pairs of layers 35, 36, such as 35A, 36A, 35B, 36B, to surface layer 38 and top surface 33. As seen in FIG. 3, in preferred embodiments, fecal material retaining structure 30 is typically thicker than absorbent core 26. Accordingly, the overall thickness of absorbent article 8 at fecal material retaining structure 30 is typically greater than the overall thickness of the absorbent article at absorbent core 26.

In use, fecal material retaining structure 30 contacts the body of the user at outer surface 33. Fecal material retaining structure 30 is resiliently compressible, and can readily bend and otherwise flex to conform to contours of the body of the user, as well as to movement by the user which exerts generally compressive and bending forces on the fecal material retaining structure. Especially bending adjustments to the shape of the fecal material retaining structure are facilitated by and at smaller apertures 32S. Thus, fecal material retaining structure 30 readily conforms and adjusts to changes in the shape of the body of the user, as well as related pressures, while retaining volumetric holding capacity to retain the fecal material received in especially the large apertures 32L.

Total containment volumes at rest and at normal usage (0.4 to 0.5 pounds per square inch compressive force on outer surface 33) are shown in the following table for a retaining structure 30 having 3 large apertures 32L having diameters of 1.5 inch (17 apertures total, 6 surge layers and 6 pulp layers) and for a retaining structure 30 having 2 large apertures 32L having diameters of 2 inches (8 apertures total, only 4 surge layers and 4 pulp layers). Thicknesses of individual surge layers and pulp layers in the respective retaining structures were all the same.

Volume Data

|  | For 3 Largest Apertures of Embodiment having 17 Apertures | For 2 Largest Apertures of Embodiment having 8 Apertures |
| --- | --- | --- |
| Total Containment Volume at rest | 61.81 cc.* | 41.09 cc. |
| Total Containment Volume at 0.5 PSI | 31.63 cc. | 13.50 cc. |

*cc = cubic centimeters.

As shown above, the data shows that the embodiment having three large apertures retains more of the rest containment volume at the three apertures than the embodiment having two large apertures. While a containment volume 46L of about 20 cubic centimeters per large aperture 32L is preferred, containment volumes 46L between about 14 cubic centimeters and about 26 cubic centimeters can also store sufficient quantities of fecal material to satisfy the objectives of the invention, depending on the respective number of large apertures 32L. When fewer apertures 32L are utilized, the surface area of each of the fewer apertures can be increased.

The containment volume 46 of the apertures is also dependent on the thickness and number of layers 35, 36. When more layers 35, 36 are used to form fecal material retaining structure 30, the thickness of the fecal material retaining structure increases and the volume 46 of the containment apertures also increases. Likewise, by reducing the number of, or thickness of layers 35, 36 used to form fecal material retaining structure 30, the containment volume of the large apertures 32L and other apertures is reduced.

There is a tradeoff between containment volume and comfort. As the number of, and especially the size of large apertures 32L increases, the absorbent article better conforms to the body of the user. However, if the surface area and diameter of large apertures 32L becomes too great, the large apertures can collapse under normal usage, such as 0.5 PSI, and the storage or containment volume thereby decreases significantly. In such an instance, the storage or containment volume of large apertures having a smaller diameter and surface area can contain more fecal material under pressure than the larger sized apertures, As the size of absorbent article 8 increases to fit various users, the width of fecal material retaining structure 30 increases to provide more containment volume for fecal material.

While leg cuffs and containment flaps are not shown or disclosed, it is contemplated that the invention can be utilized with any known leg cuff structure or containment flap structure mounted to absorbent article 8.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

Having thus described the invention, what is claimed is:

1. A fecal material retaining structure for mounting on a chassis of an absorbent article which is to be worn on a body of a wearer, said fecal material retaining structure comprising:

(a) a surface layer having a first surface, and a second surface which opposes the first surface;

(b) at least one first layer made of a first material, wherein said at least one first layer has a third surface, and a fourth surface which opposes the third surface, said third surface of said at least one first layer being secured to said first surface of said surface layer;

(c) at least one second layer made of a second material wherein said at least one second layer has a fifth surface, and a sixth surface which opposes the fifth surface, said fifth surface of said at least one second layer being secured to said fourth surface of said first layer; and (d) at least two apertures formed through all of said surface layer, said at least one first layer, and said at least one second layer, said at least two apertures being configured to have a minimum depth of at least about 0.38 inch and a maximum depth of larger than 1.0 inch and to have an overall surface area from about 25% to about 75% of a fecal material retaining structure as defined within an outer perimeter of said fecal material retaining structure to receive and retain a solids portion of fecal material and any liquids immobilized therein when said fecal material retaining structure is mounted on the absorbent article and worn by the wearer of the absorbent article and wherein said at least two apertures are adapted to displace the solids portion of fecal material and any liquid immobilized therein from skin of the wearer of the absorbent article to prevent the solids portion of the fecal material and any liquid immobilized therein from spreading outwardly along an outside surface of said fecal material retaining structure to cover an increased surface area of the skin of the wearer of the absorbent article.

2. The fecal material retaining structure as in claim 1, said surface layer having a critical surface tension for wetting, said surface layer critical surface tension for wetting being less than a critical surface tension for wetting of fecal material from a breast fed infant.

3. The fecal material retaining structure as in claim 1, said surface layer having a critical surface tension for wetting, said critical surface tension for wetting being less than about 50 dynes/centimeter, which is effective to assist with moving the fecal material into said at least two apertures.

4. The fecal material retaining structure as in claim 1, wherein said at least one first layer of first material includes cellulosic pulp.

5. The fecal material retaining structure as in claim 1, wherein said at least one second layer of second material includes resilient surge material.

6. The fecal material retaining structure as in claim 1, said at least one first layer comprising first multiple layer elements and said at least one second layer comprising second multiple layer elements, said first and second multiple layer elements being interleaved and secured to one another.

7. An absorbent article for being worn on a body of a wearer, said absorbent article having a length, a width, a front portion, a rear portion, a crotch portion connecting said front and rear portions, and a central axis perpendicular to the length of said absorbent article, the central axis extending across said crotch portion and dividing said absorbent article into two sections of approximately equal length, said absorbent article comprising:
  (a) a chassis comprising:
    (i) an outer cover, and
    (ii) a bodyside liner mounted in facing relationship to said outer cover and adapted to contact skin of the body of the wearer of said absorbent article in said front portion of said absorbent article;
  (b) an absorbent core located between said bodyside liner and said outer cover in said front portion of said absorbent article; and
  (c) a fecal material retaining structure for retaining a solids portion of fecal material and any liquid immobilized therein to prevent the solids portion of the fecal material and any liquid immobilized therein from spreading outwardly along an outside surface of said bodyside liner and thereby covering an increased area of the skin of the body of the wearer of said absorbent article, said fecal material retaining structure being mounted in said rear portion of said absorbent article, said fecal material retaining structure having a depth, and at least two apertures configured to have a minimum depth of at least about 0.38 inch and a maximum depth of larger than 1.0 inch and an ovefall surface area from about 25% to about 75% of a fecal material retaining structure surface area as defined within an outer perimeter of said fecal material retaining structure and extending through at least a partial thickness of said fecal material retaining structure, said at least two apertures defining sufficient volume and structure to receive and retain therein an amount of the solids portion of the fecal material and any liquid immobilized therein representing a typical bowel movement of a typical user.

8. The absorbent article as in claim 7, said fecal material retaining structure comprising at least first and second layers of respective first and second materials.

9. The absorbent article as in claim 8, said fecal material retaining structure extending from about 0.5 inch to about 2 inches frontwardly of the central axis.

10. The absorbent article as in claim 7, said at least two apertures of said fecal material retaining structure having a combined overall volume capacity for receiving and storing fecal material of at least 140 cubic centimeters at rest.

11. The absorbent article as in claim 7, said at least two apertures being configured and arranged such that said retaining structure readily flexes at any one or more of said at least two apertures to conform to the body of the wearer of said absorbent article.

12. The absorbent article as in claim 7, at least one of said at least two apertures having a depth at rest of at least about 0.5 inch.

13. The absorbent article as in claim 7, further comprising a body contactable surface of said absorbent article, wherein in said front portion of said absorbent article, said body contactable surface is dominantly comprised of said bodyside liner, and wherein in said rear portion of said absorbent article, said body contactable surface is not dominantly comprised of said bodyside liner.

14. The absorbent article as in claim 7, further comprising a body contactable surface of said absorbent article, wherein in said rear portion of said absorbent article, said body contactable surface is dominantly comprised of said fecal material retaining structure, and wherein in said front portion of said absorbent article, said body contactable surface is not dominantly comprised of said fecal material retaining structure.

15. The absorbent article as in claim 7, wherein at least one of said at least two apertures of said fecal material retaining structure is larger than at least one of the other said at least two apertures, said larger aperture having a surface area of at least 5 square centimeters.

16. The absorbent article as in claim 15 wherein at least one of said at least two apertures is a smaller aperture having a surface area of less than about 5 square centimeters, said at least one smaller aperture providing enhanced flexibility to said fecal material retaining structure.

17. The absorbent article as in claim 14, a common longitudinal axis extending through the front portion, the rear portion, and the crotch portion along the length of said absorbent article, said at least one smaller aperture being displaced from said longitudinal axis.

18. The absorbent article as in claim 7, wherein edges of said fecal material retaining structure are adapted to be in direct contact with the body of the wearer of said absorbent article at said at least two apertures.

* * * * *